United States Patent
Chiang et al.

(10) Patent No.: US 9,398,971 B2
(45) Date of Patent: Jul. 26, 2016

(54) HINGE FOR AN ORTHOPEDIC BRACE

(71) Applicant: Plus Meditech Co., Ltd., Tainan (TW)

(72) Inventors: Yueh-Hua Chiang, Taipei (TW); Fu-Lin Chuang, Tainan (TW)

(73) Assignee: Plus Meditech Co., Ltd., Tainan (TW)

( * ) Notice: Subject to any disclaimer, the term of this patent is extended or adjusted under 35 U.S.C. 154(b) by 323 days.

(21) Appl. No.: 14/206,595

(22) Filed: Mar. 12, 2014

(65) Prior Publication Data

US 2015/0141888 A1    May 21, 2015

(30) Foreign Application Priority Data

Nov. 19, 2013 (TW) .............................. 102142046 A

(51) Int. Cl.
*A61F 5/00* (2006.01)
*A61F 5/01* (2006.01)
(52) U.S. Cl.
CPC .............. *A61F 5/0123* (2013.01); *A61F 5/0125* (2013.01); *A61F 2005/0137* (2013.01); *A61F 2005/0165* (2013.01); *A61F 2005/0181* (2013.01)
(58) Field of Classification Search
CPC ........... A61F 2005/0165; A61F 5/0123; A61F 2005/0137; A61F 2005/0169; A61F 2005/0179; A61F 2005/0181; A61F 5/0125; Y10T 403/32606; Y10T 403/32811
USPC .................................. 602/16, 20–28; 128/882
See application file for complete search history.

(56) References Cited

U.S. PATENT DOCUMENTS

| | | | | |
|---|---|---|---|---|
| 7,235,059 B2* | 6/2007 | Mason | ................... | A61F 5/0125 128/882 |
| 7,762,972 B2* | 7/2010 | Cho | ...................... | A61F 5/0123 602/16 |
| 7,833,181 B2* | 11/2010 | Cormier | ................ | A61F 5/0125 128/882 |
| 2009/0018476 A1* | 1/2009 | Cho | ...................... | A61F 5/0123 602/16 |
| 2013/0253396 A1* | 9/2013 | Chetlapalli | ........... | A61F 5/0125 602/16 |

FOREIGN PATENT DOCUMENTS

TW    EP 2873394 A1 *    5/2015    ............ A61F 5/0125

* cited by examiner

*Primary Examiner* — Michael Brown
(74) *Attorney, Agent, or Firm* — Muncy, Geissler, Olds & Lowe, P.C.

(57) ABSTRACT

A hinge for an orthopedic brace includes: a pivot shaft; a lower leg plate pivoted to the pivot shaft; an upper leg plate; a catch plate having a toothed peripheral edge; and two position adjusting units, each of which includes a rotatable limiting seat, a limiting pin, and a slider body. The rotatable limiting seat defines a housing chamber therein, and is formed with a wall slot. The slider body is slidably disposed in the housing chamber. The limiting pin extends from the slider body through the wall slot for engaging and disengaging the toothed peripheral edge. The catch plate is formed with a guiding groove. The rotatable limiting seat has a tongue protruding into the guiding groove.

9 Claims, 16 Drawing Sheets

HINGE FOR AN ORTHOPEDIC BRACE

CROSS-REFERENCE TO RELATED APPLICATION

This application claims priority of Taiwanese Application No. 102142046, filed on Nov. 19, 2013.

BACKGROUND OF THE INVENTION

1. Field of the Invention

This invention relates to a hinge for an orthopedic brace, more particularly to a hinge for an orthopedic brace including a rotatable limiting seat and a slider body mounted in the limiting seat.

2. Description of the Related Art

U.S. Pat. No. 7,235,059 discloses a conventional hinge for an orthopedic brace. The conventional hinge includes upper and lower arms, first and second rotation plates, a pivotal connector connecting the first and second rotation plates, and a rotation limiting mechanism for limiting an angle between the first and second rotation plates. The rotation limiting mechanism includes a series of rotation limiting teeth that are formed on peripheral edges of the first and second rotation plates, a flexion rotation limiting assembly, and an extension rotation limiting assembly. Each of the flexion and extension rotation limiting assemblies has a stop post, and upper and lower lateral heads that extend laterally and respectively from top and bottom ends of the stop post and that are anchored on the peripheral edges of the first and second rotation plates, such that the first and second rotation plates are disposed between the upper and lower lateral heads in an axial direction. Each of the flexion and extension rotation limiting assemblies further has a rotation limiting assembly plate, a leaf spring, and upper and lower lateral engagement faces. The rotation limiting assembly plate extends laterally from a middle of the stop post, is disposed between the first and second rotation plates, and is formed with a spring cut-out for mounting of the leaf spring therein and for extension of the pivotal connector therethrough. The leaf spring is frictionally sleeved on the pivot connector. The upper lateral engagement face is formed on the stop post at a position between the top end and the middle of the stop post, and is engageable with selected ones of the rotation limiting teeth on the first rotation plate. The lower lateral engagement face is formed on the stop post at a position between the bottom end and the middle of the stop post, and is engageable with selected ones of the rotation limiting teeth on the second rotation plate.

Since the upper and lower lateral heads are disposed at outer sides of the first and second rotation plates along the axial direction of the pivot connector, the overall thickness of the conventional hinge in the axial direction is considerably increased. In addition, since the leaf spring is in contact with the pivotal connector, rotation of the leaf spring about the pivotal connector may cause wear type damage to the leaf spring and/or the pivotal connector.

SUMMARY OF THE INVENTION

Therefore, an object of the present invention is to provide a hinge for orthopedic brace that can overcome the aforesaid drawbacks associated with the prior art.

According to the present invention, there is provided a hinge for an orthopedic brace. The hinge comprises: a pivot shaft; a lower leg plate pivoted to the pivot shaft; an upper leg plate; a catch plate secured to an end portion of the upper leg plate and having an annular portion that is sleeved around the pivot shaft and that has a toothed peripheral edge; and two position adjusting units, each of which includes a rotatable limiting seat, a limiting pin, and a slider body. The rotatable limiting seat is mounted rotatably on the catch plate, and has a seat housing that defines a housing chamber therein and that is formed with a wall slot which extends in a radial direction with respect to the pivot shaft. The slider body is slidably disposed in the housing chamber, and is slidable relative to the seat housing in the radial direction between engaging and disengaging positions. The limiting pin extends outwardly of the housing chamber from the slider body through the wall slot so as to be co-slidable with the slider body relative to the seat housing. The limiting pin of each of the position adjusting units engages the toothed peripheral edge when the slider body is disposed at the engaging position, thereby preventing rotation of the position adjusting unit relative to the catch plate about the pivot shaft, and is disengaged from the toothed peripheral edge when the slider body is disposed at the disengaging position, thereby permitting rotation of the position adjusting unit about the pivot shaft. The annular portion of the catch plate is formed with two circumferentially extending guiding grooves. The rotatable limiting seat of each of the position adjusting units further has a tongue that protrudes from the seat housing into a respective one of the circumferentially extending guiding grooves, so that rotation of each of the rotatable limiting seats about the pivot shaft is guided along the respective one of the circumferentially extending guiding grooves.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
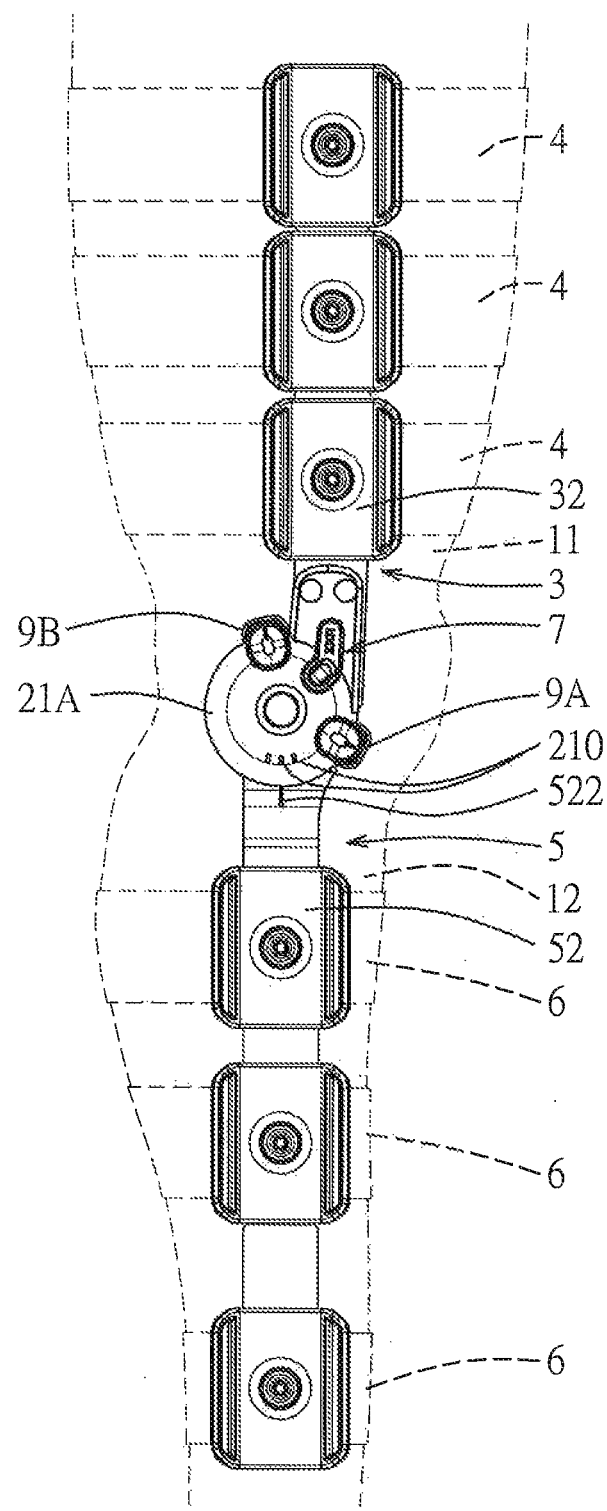
FIG. 1 is a schematic side view of the preferred embodiment of a hinge for an orthopedic brace according to the present invention.
Figure 2:
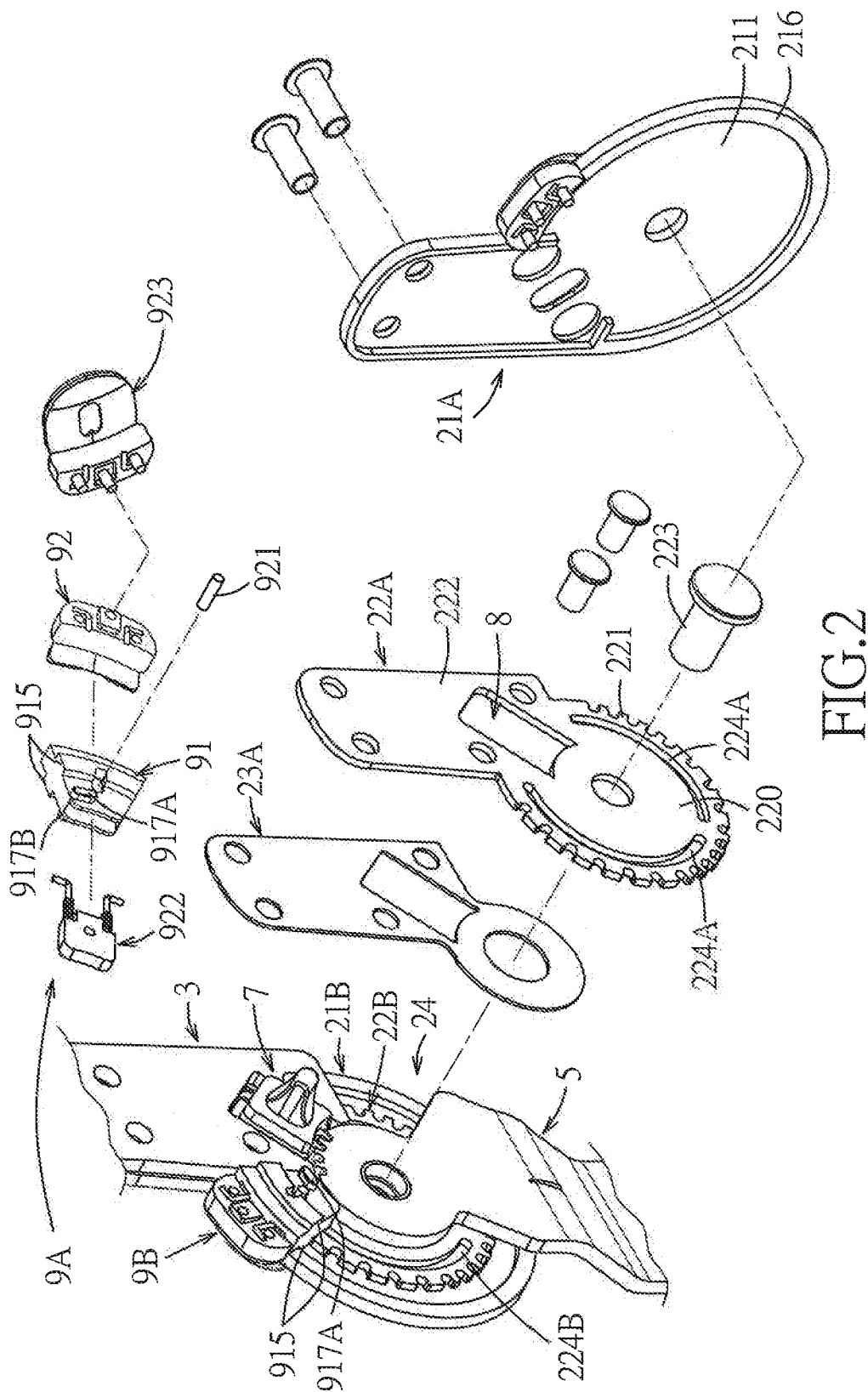
FIG. 2 is a fragmentary exploded perspective view of the preferred embodiment.
Figure 3:
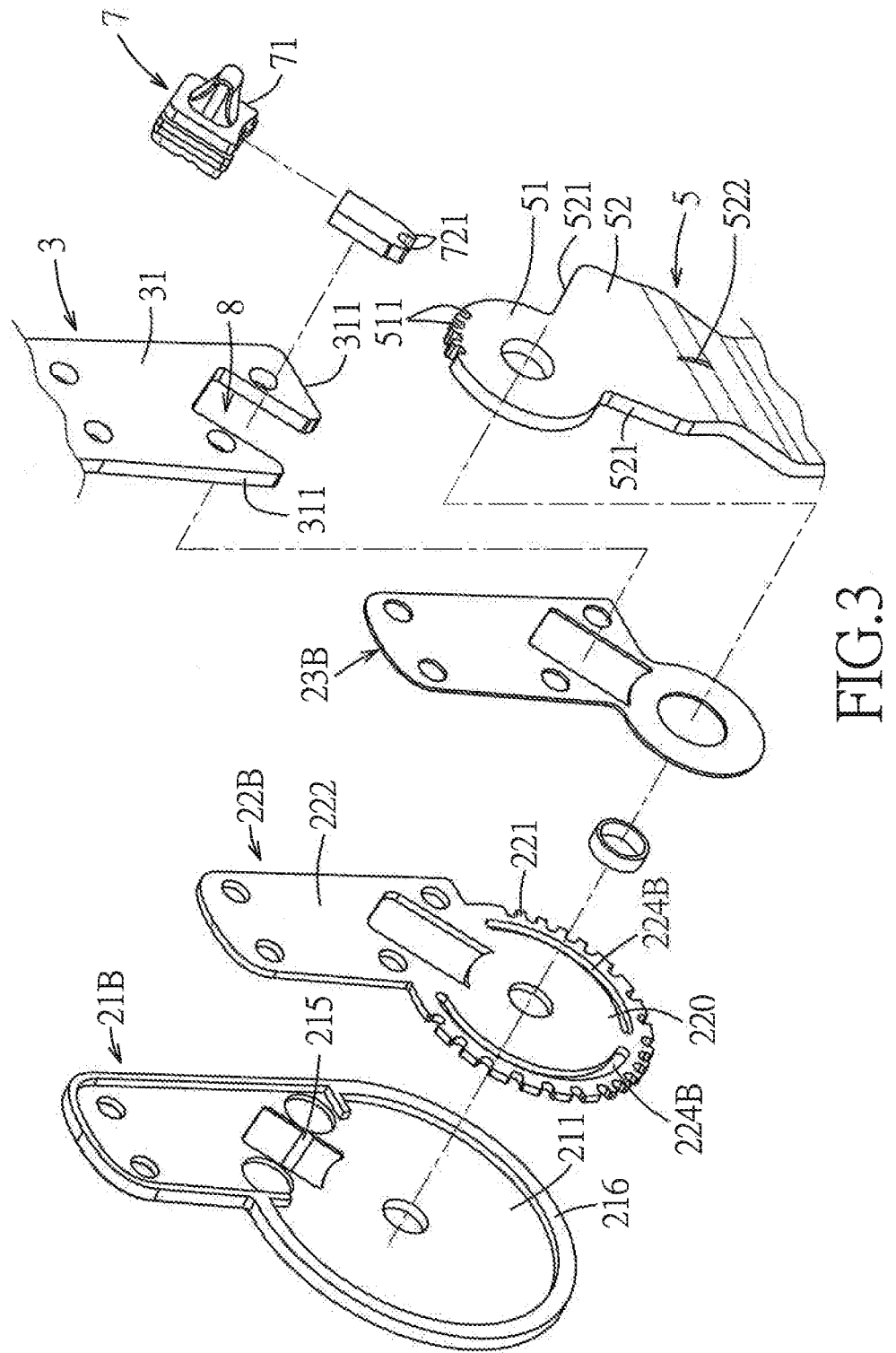
FIG. 3 is a fragmentary exploded perspective view of a portion of the preferred embodiment.
Figure 4:
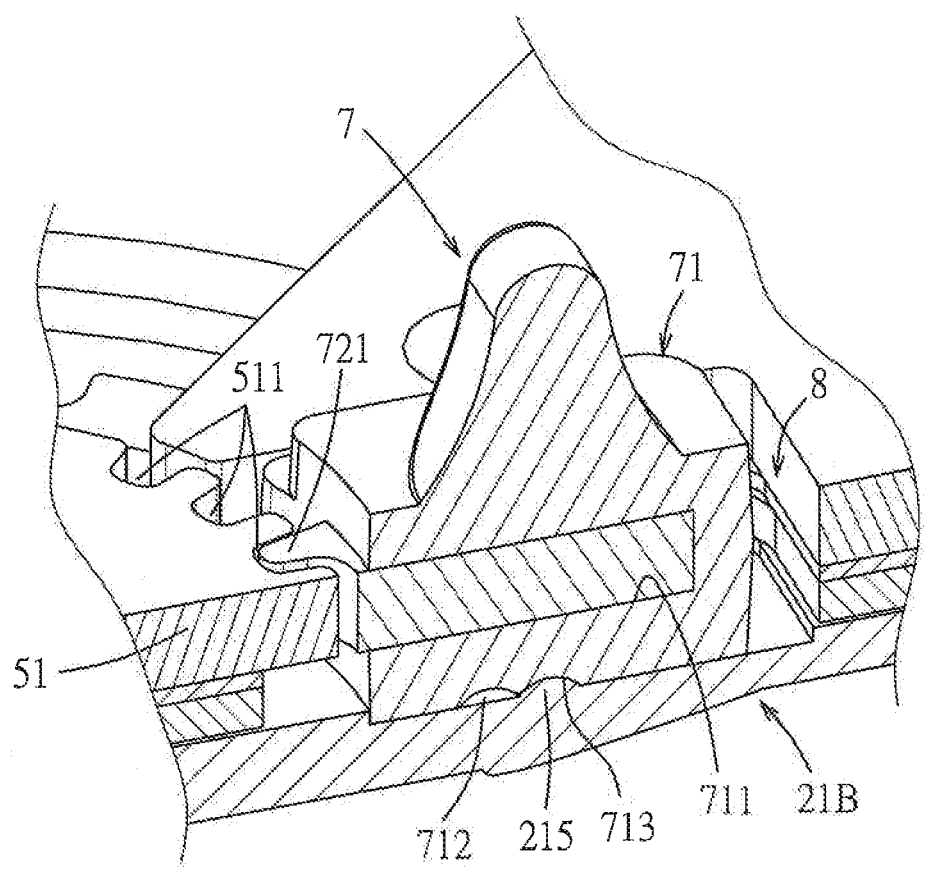
FIG. 4 is a fragmentary sectional view of a lock mechanism of the preferred embodiment.
Figure 5:
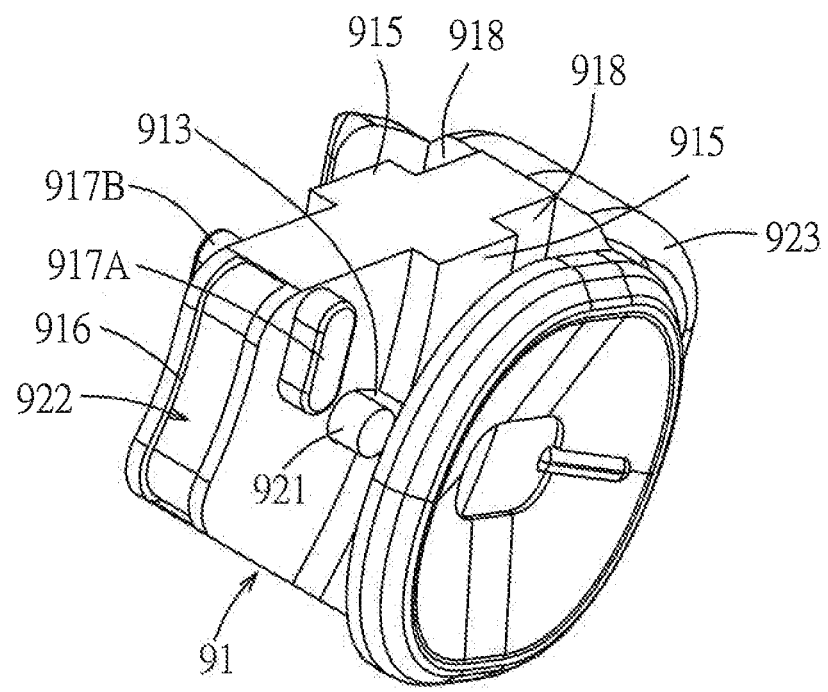
FIG. 5 is a perspective view of a position adjusting unit of the preferred embodiment.
Figure 6:
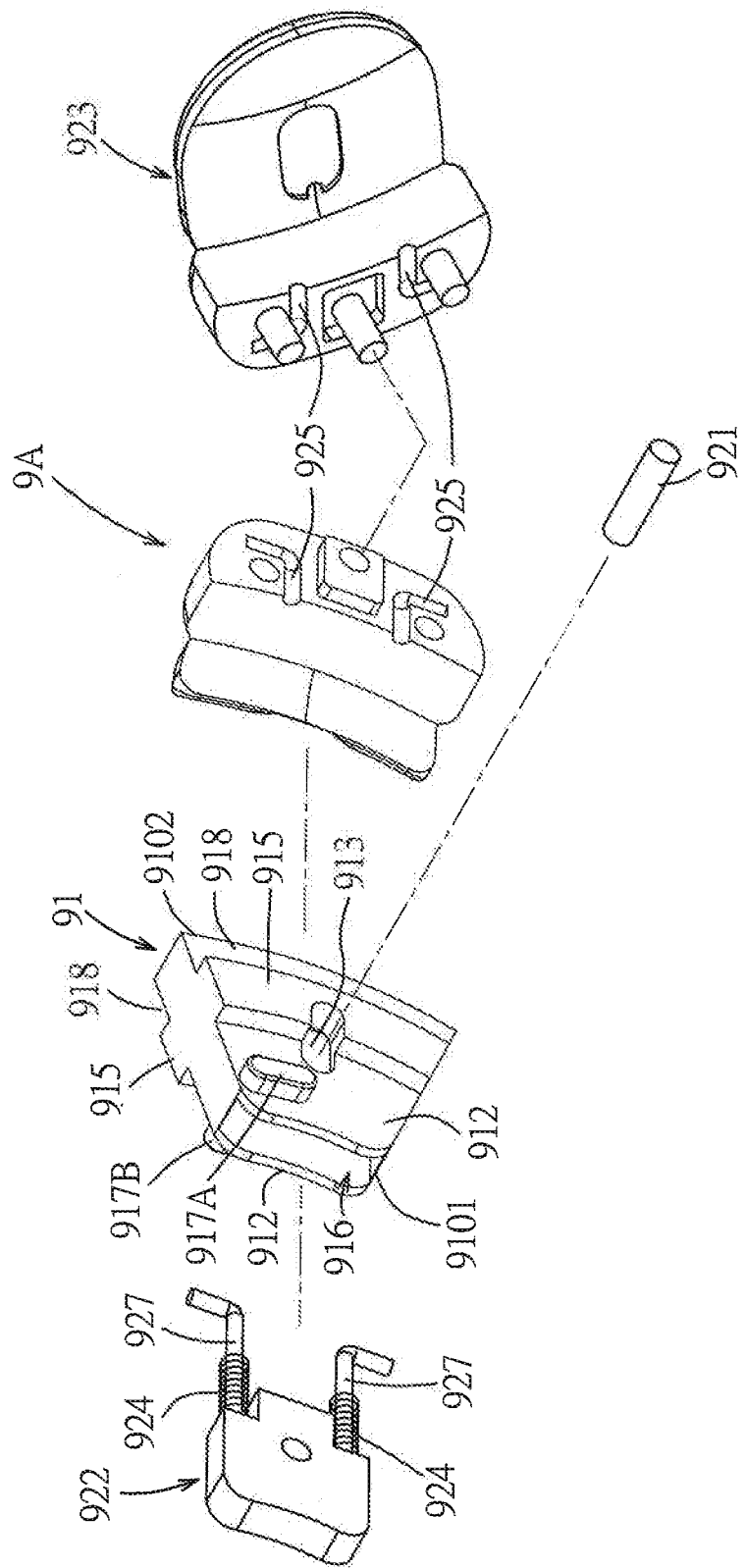
FIG. 6 is an exploded perspective view of the position adjusting unit of the preferred embodiment.
Figure 7:
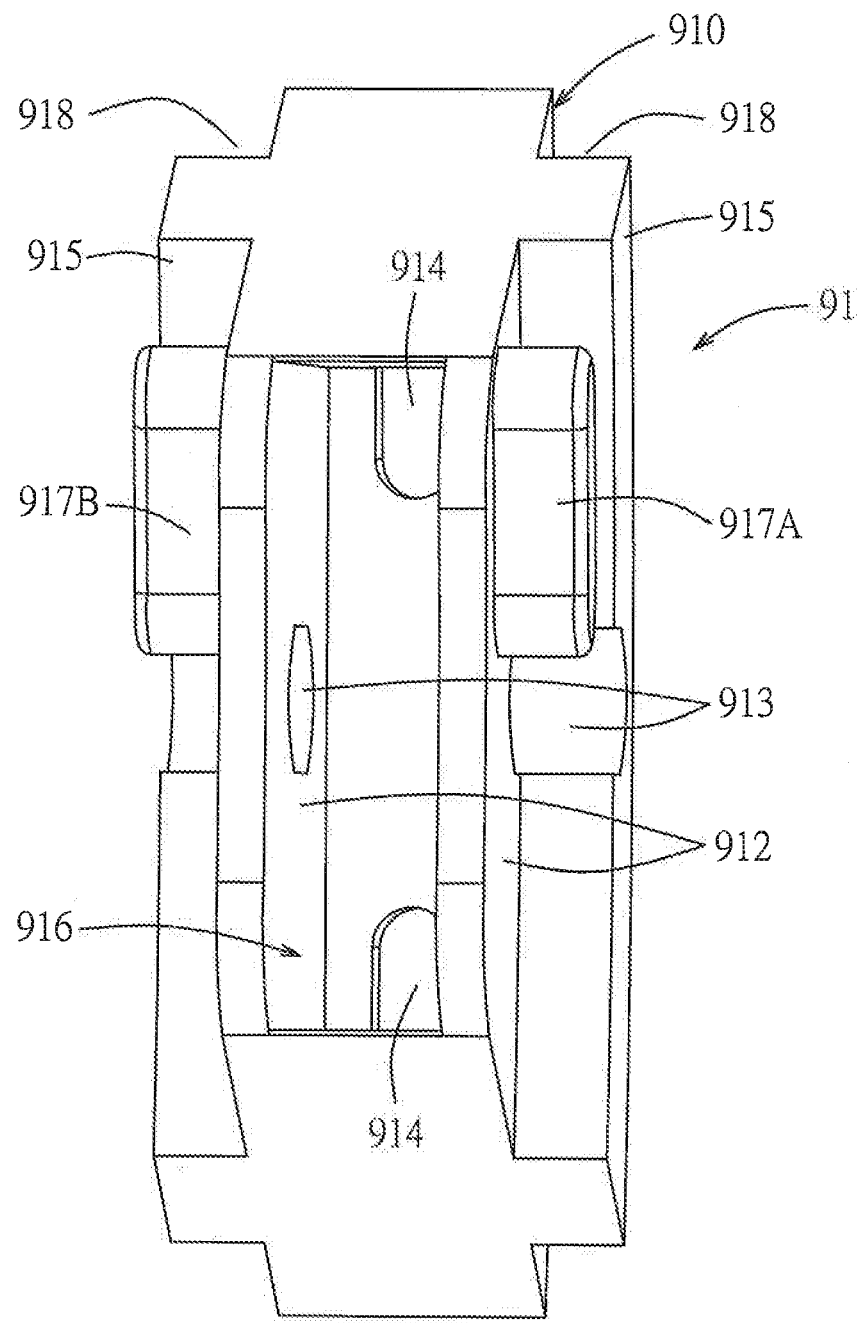
FIG. 7 is a side view of the position adjusting unit of the preferred embodiment.
Figure 8:
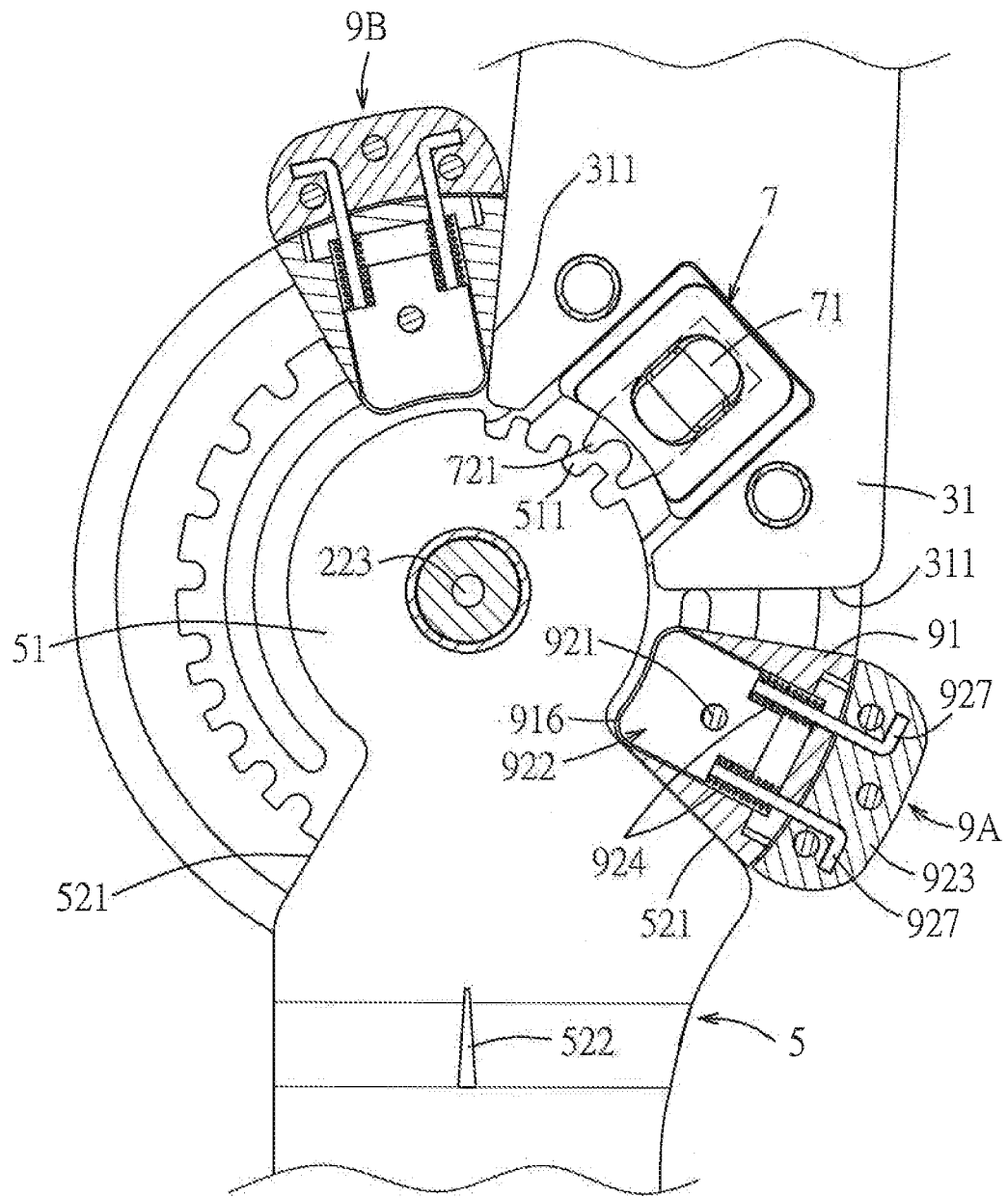
FIG. 8 is a fragmentary partly sectional view of the preferred embodiment illustrating a state where a latch bar is disposed at an unlocked position and a slider body is disposed at an engaging position.

FIGS. 1 to 8 illustrate the preferred embodiment of a hinge for an orthopedic brace according to the present invention. The orthopedic brace includes a plurality of upper wearing bands 4 and a plurality of lower wearing bands 6. The hinge includes a pivot shaft 223, upper and lower leg plates 3, 5, first and second covers 21A, 21B, first and second catch plates 22A, 22B, first and second buffering pads 23A, 23B, first and second position adjusting units 9A, 9B, and a lock mechanism 7.

Each of the first and second catch plates 22A, 22B has an annular portion 220, and a securing fin portion 222 that extends from the annular portion 220 and that is secured to an end portion 31 of the upper leg plate 3 through fastening means. The annular portion 220 is sleeved around the pivot shaft 223, and has a toothed peripheral edge 221. The annular portions 220 of the first and second catch plates 22A, 22B are coaxially disposed, and cooperate with each other to define an insertion gap 24 therebetween.

The lower leg plate 5 has an annular end portion 51 that is pivoted to the pivot shaft 223, and a leg extension portion 52 that is formed with an indicator mark 522, that extends from the annular end portion 51 and that has two first limiting side edges 521 which are angularly spaced apart from each other. The annular end portion 51 of the lower leg plate 5 is disposed in the insertion gap 24. Each of the first and second buffering pads 23A, 23B is sandwiched between the annular end portion 51 of the lower leg plate 5 and the annular portion 220 of a respective one of the first and second catch plates 22A, 22B. The lower wearing bands 6 are secured to the extension portion 52 for circling tightly around a lower leg 12 of a user.

The end portion 31 of the upper leg plate 3 is formed with a notch 8, has two second limiting side edges 311, and extends into the insertion gap 24. The notch 8 extends from an inner closed end thereof in a radial direction with respect to the pivot shaft 223 toward the annular end portion 51 of the lower leg plate 5. The upper leg plate 3 further has an extension 32 that extends from the end portion 31 of the upper leg plate 3. The upper wearing bands 4 are secured to the extension 32 of the upper leg plate 3 for circling tightly around a thigh 11 of the user.

The first and second covers 21A, 21B are secured to the end portion 31 of the upper leg plate 3 through the fastening means so as to cover the first and second catch plates 22A, 22B. Each of the first and second covers 21A, 21B has an annular portion 211, and a rim portion 216 which protrudes from the annular portion 211 in an axial direction with respect to the pivot shaft 223. The annular portions 211 of the first and second covers 21A, 21B are coaxially disposed with each other, and sandwich the first and second catch plates 22A, 22B therebetween. The first cover 21A is formed with a plurality of angularly displaced indicia 210.

Figure 11:
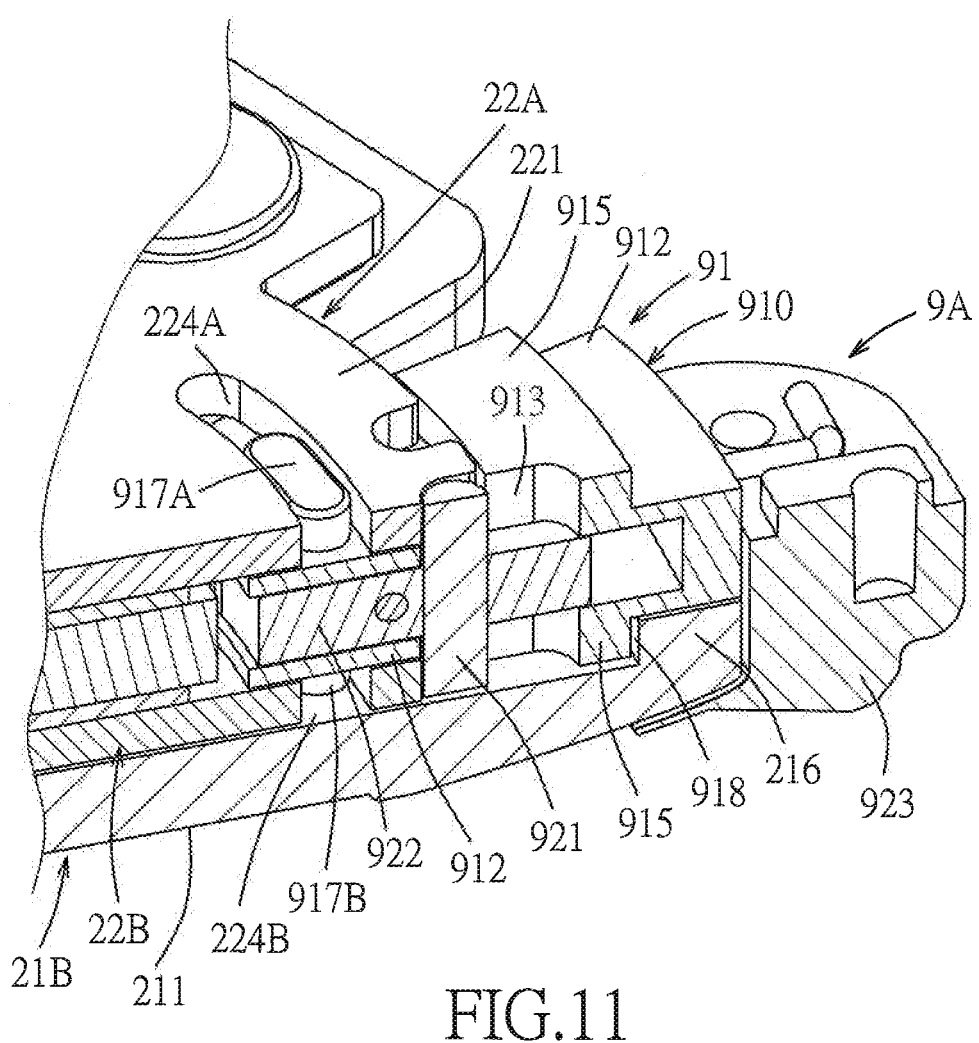
FIG. 11 is a fragmentary sectional view of the preferred embodiment illustrating the state where the slider body is disposed at the engaging position.
Figure 12:
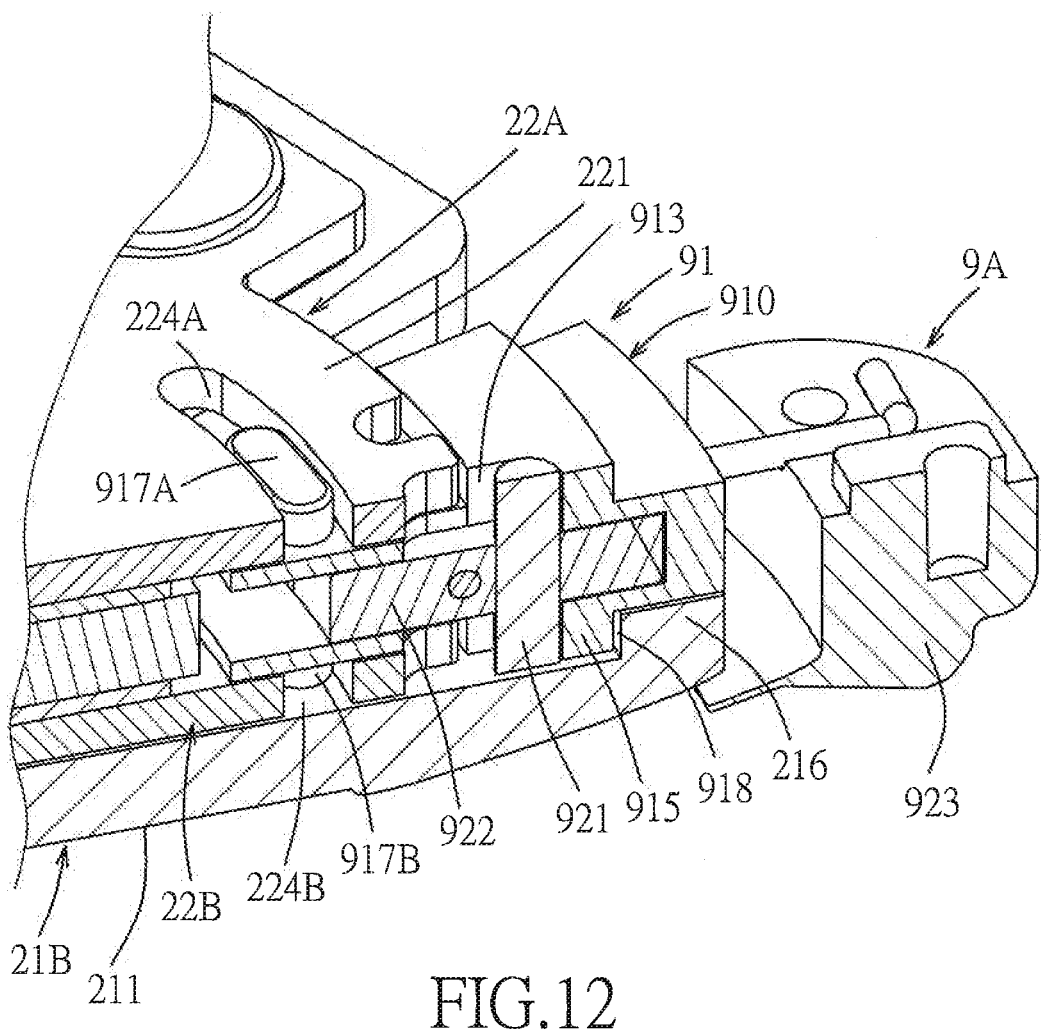
FIG. 12 is a fragmentary sectional view of the preferred embodiment illustrating a state where the slider body is disposed at a disengaging position.
Figure 13:
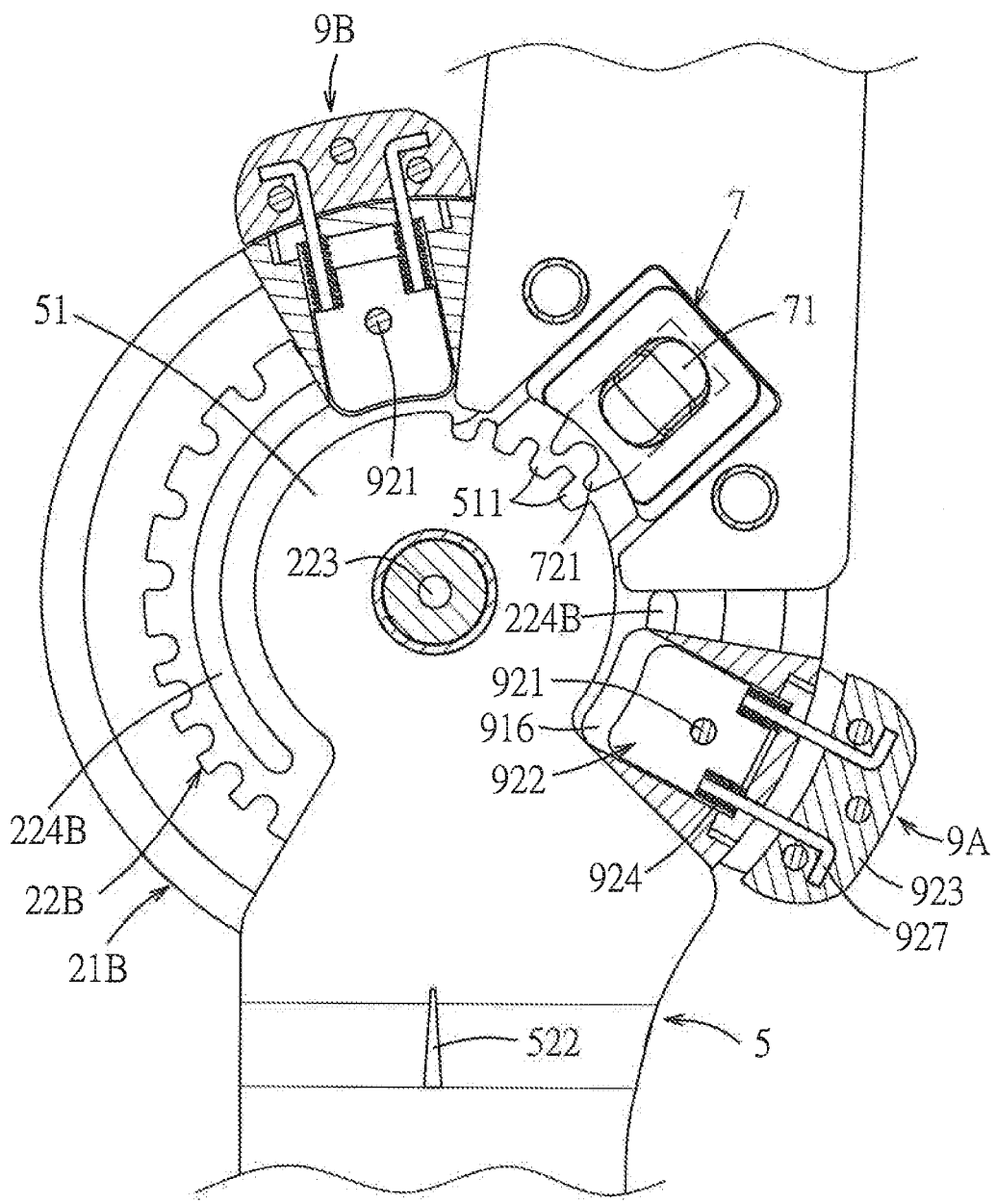
FIG. 13 is a fragmentary partly sectional view of the preferred embodiment illustrating another state where the latch bar is disposed at the unlocked position and the slider body is disposed at the disengaging position.
Figure 14:
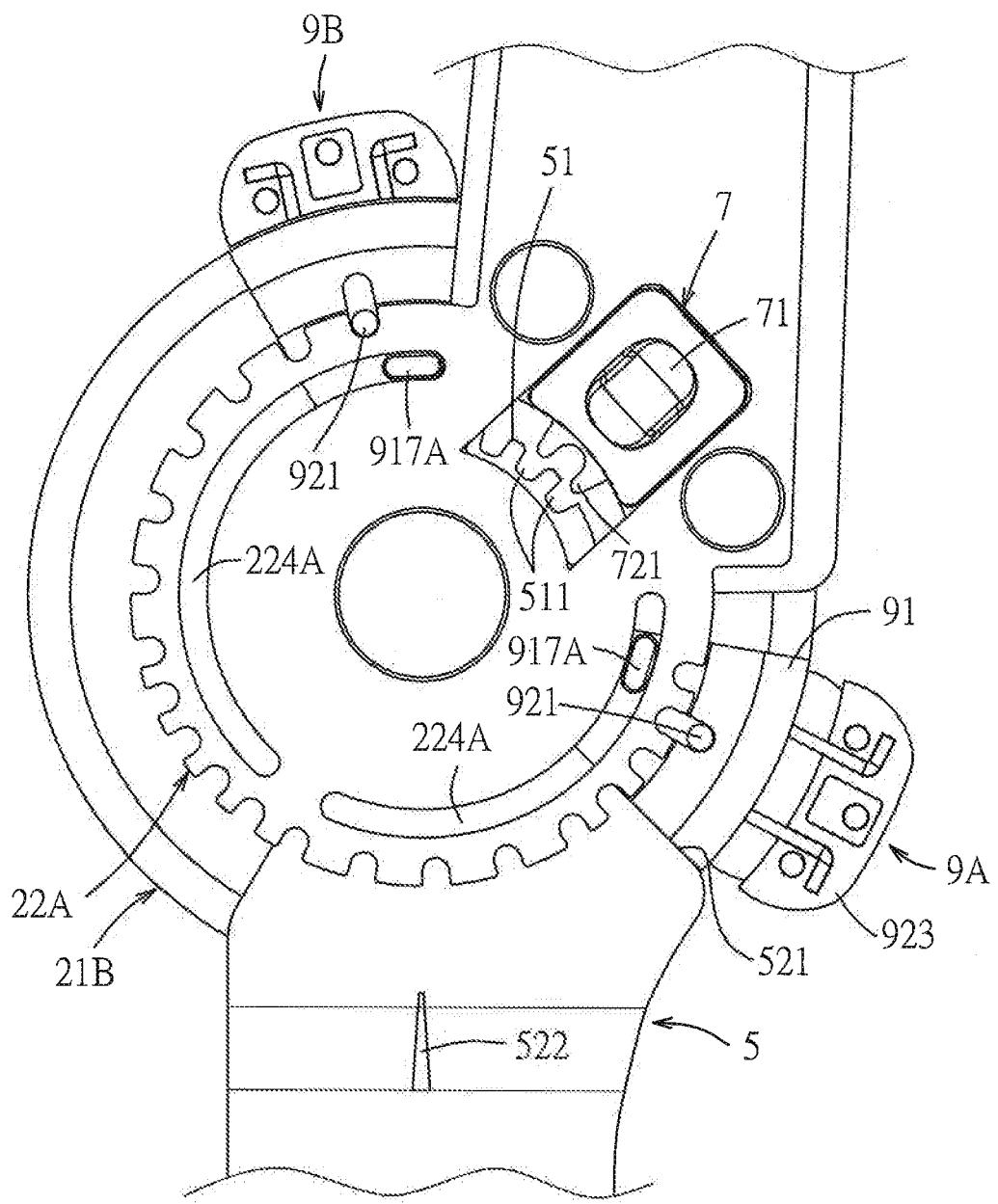
FIGS. 14 to 16 are fragmentary side views of the preferred embodiment illustrating consecutive steps of how the rotational range of the lower leg plate is adjusted by moving the first position adjusting unit from a first angular position to a second angular position.

Each of the first and second position adjusting units 9A, 9B includes a rotatable limiting seat 91, a limiting pin 921, a slider body 922, a pair of connecting rods 927, a pair of coil springs 924, and a pull knob 923. Since the first and second position adjusting units 9A, 9B have a similar structure, only one of them will be described in detail hereinafter for the sake of brevity. The rotatable limiting seat 91 is mounted rotatably on the first and second catch plates 22A, 22B, and has a seat housing 910 that defines a housing chamber 916 therein and that is formed with a wall slot 913 which extends in the radial direction with respect to the pivot shaft 223. The slider body 922 is slidably disposed in the housing chamber 916, and is slidable relative to the seat housing 910 in the radial direction between engaging and disengaging positions (see FIGS. 11 and 12). The limiting pin 921 extends outwardly of the housing chamber 916 from the slider body 922 through the wall slot 913 in the axial direction, and is co-slidable with the slider body 922 relative to the seat housing 910. The limiting pin 921 engages the toothed peripheral edges 221 of the first and second catch plates 22A, 22B when the slider body 922 is disposed at the engaging position, thereby preventing rotation of the first and second position adjusting units 9A, 9B relative to the first and second catch plates 22A, 22B about the pivot shaft 223, and is disengaged from the toothed peripheral edges 221 when the slider body 922 is disposed at the disengaging position, thereby permitting rotation of the first and second position adjusting units 9A, 9B about the pivot shaft 223. The annular portion 220 of the first catch plate 22A is formed with two first circumferentially extending guiding grooves 224A. The annular portion 220 of the second catch plate 22B is formed with two second circumferentially extending guiding grooves 224B corresponding to the first circumferentially extending guiding grooves 224A, respectively. The rotatable limiting seat 91 of each of the first and second position adjusting units 9A, 9B further has first and second tongues 917A, 917B that protrude from the seat housing 910 respectively into one of the first circumferentially extending guiding grooves 224A and a corresponding one of the second circumferentially extending guiding grooves 224B, so that rotation of each of the first and second position adjusting units 9A, 9B about the pivot shaft 223 is guided along a corresponding pair of the first and second circumferentially extending guiding grooves 224A, 224B.

The seat housing 910 of each of the rotatable limiting seats 91 has inner and outer radial ends 9101, 9102, two opposite radially extending side walls 912 that extend between the inner and outer radial ends 9101, 9102, and two curved bar strips 915 that protrude from and that cooperate with the side walls 912 to define two limiting recesses 918 therebetween. The side walls 912 are opposite to and are registered with each other along the axial direction parallel to the pivot shaft 223. The wall slot 913 is formed in and extends through the side walls 912. The rim portions 216 of the first and second covers 21A, 21B extend respectively into the limiting recesses 918 in the seat housings 910 of the rotatable limiting seats 91, and abut respectively against the bar strips 915 of the seat housings 910 of the rotatable limiting seats 91 so as to limit the rotatable limiting seats 91 against movement in the radial direction.

The pull knob 923 is disposed at and abuts against peripheral edges of the first and second covers 21A, 21B. The connecting rods 927 extend from the slider body 922 through two openings 914 in the outer end 9102 of the seat housing 910 to connect with the pull knob 923. Each of the connecting rods 927 has an L-shaped end portion that is fitted into an inner groove 925 in the pull knob 923.

The coil springs 924 are sleeved around the connecting rods 927, are disposed in the housing chamber 916, and abut against the outer end 9102 of the seat housing 910 and the slider body 922 for restoring the slider body 922 from the disengaging position to the engaging position.

The limiting side edges 521 of the lower leg plate 5 are disposed angularly between the rotatable limiting seats 91 of the first and second position adjusting units 9A, 9B, so that rotation of the lower leg plate 5 about the pivot shaft 223 is limited by the rotatable limiting seats 91.

Figure 9:
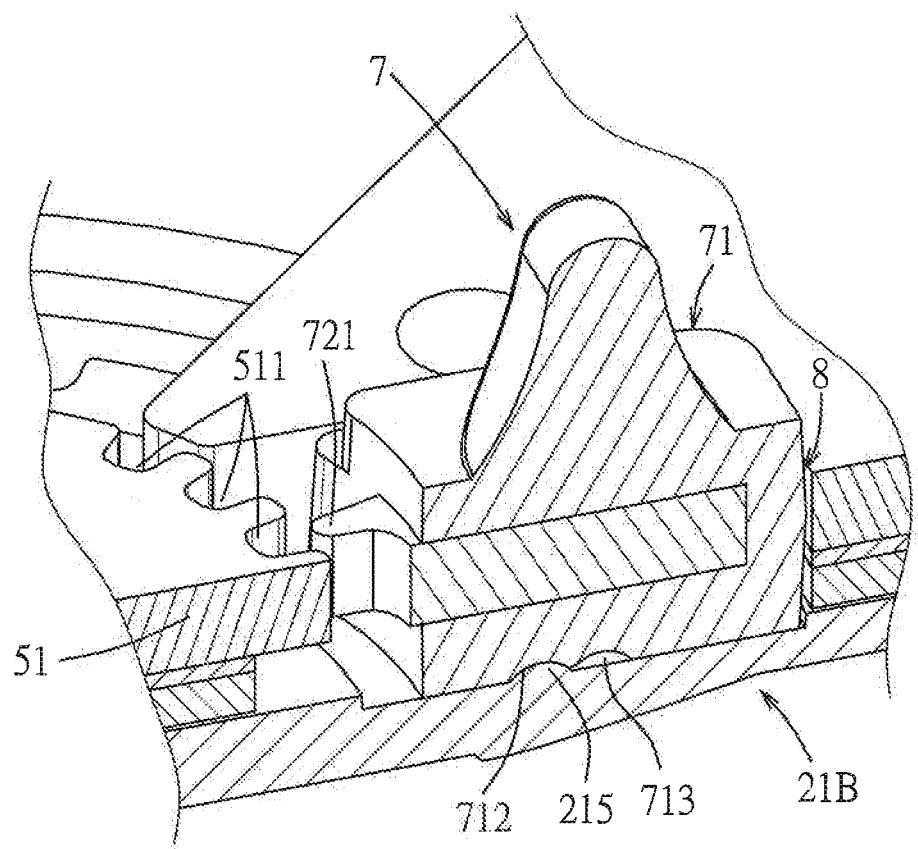
FIG. 9 is a fragmentary sectional view of the preferred embodiment illustrating the state where the latch bar is disposed at the unlocked position.
Figure 10:
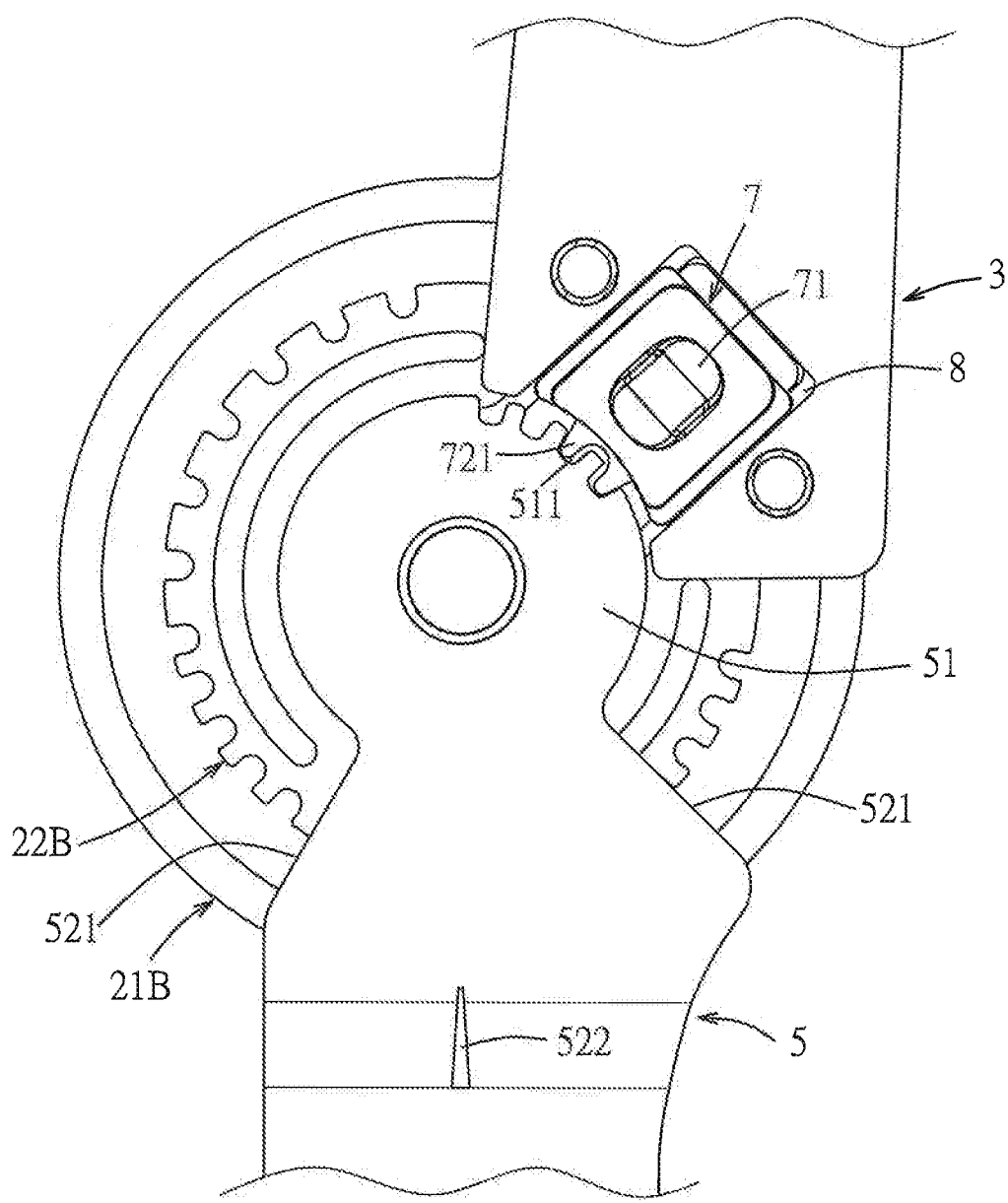
FIG. 10 is a fragmentary side view of the preferred embodiment illustrating a state where the latch bar is disposed at a locked position.

The lock mechanism 7 includes a latch bar 71 that extends into and through the notch 8 in the end portion 31 of the upper leg plate 3, and is mounted slidably on the second cover 21B. The latch bar 71 is provided with a latch protrusion 721 that is detachably inserted into a slot 711 in the latch bar 71 and that protrudes outwardly therefrom. The annular end portion 51 of the lower leg plate 5 has an annular peripheral edge that is formed with a plurality of tooth grooves 511. The latch bar 71 is slidable on the second cover 21B in the radial direction between an unlocked position (see FIGS. 8 and 9) and a locked position (see FIGS. 4 and 10). The latch protrusion 721 engages a selected one of the tooth grooves 511 when the latch bar 71 is disposed at the locked position, thereby preventing rotation of the lower leg plate 5 relative to the upper leg plate 3 about the pivot shaft 223, and is disengaged from the tooth grooves 511 when the latch bar 71 is disposed at the unlocked position, thereby permitting rotation of the lower leg plate 5 relative to the upper leg plate 3 about the pivot shaft 223.

In this embodiment, the latch bar 71 has a bottom that is formed with first and second retaining grooves 712, 713 which are arranged along the radial direction. The second cover 21B is formed with a retaining protrusion 215 that protrudes therefrom toward the bottom of the latch bar 71. The retaining protrusion 215 engages the second retaining groove 713 and is disengaged from the first retaining groove 712 when the latch bar 71 is disposed at the locked position, and engages the first retaining groove 712 and is disengaged from the second retaining groove 713 when the latch bar 71 is disposed at the unlocked position.

Figure 15:
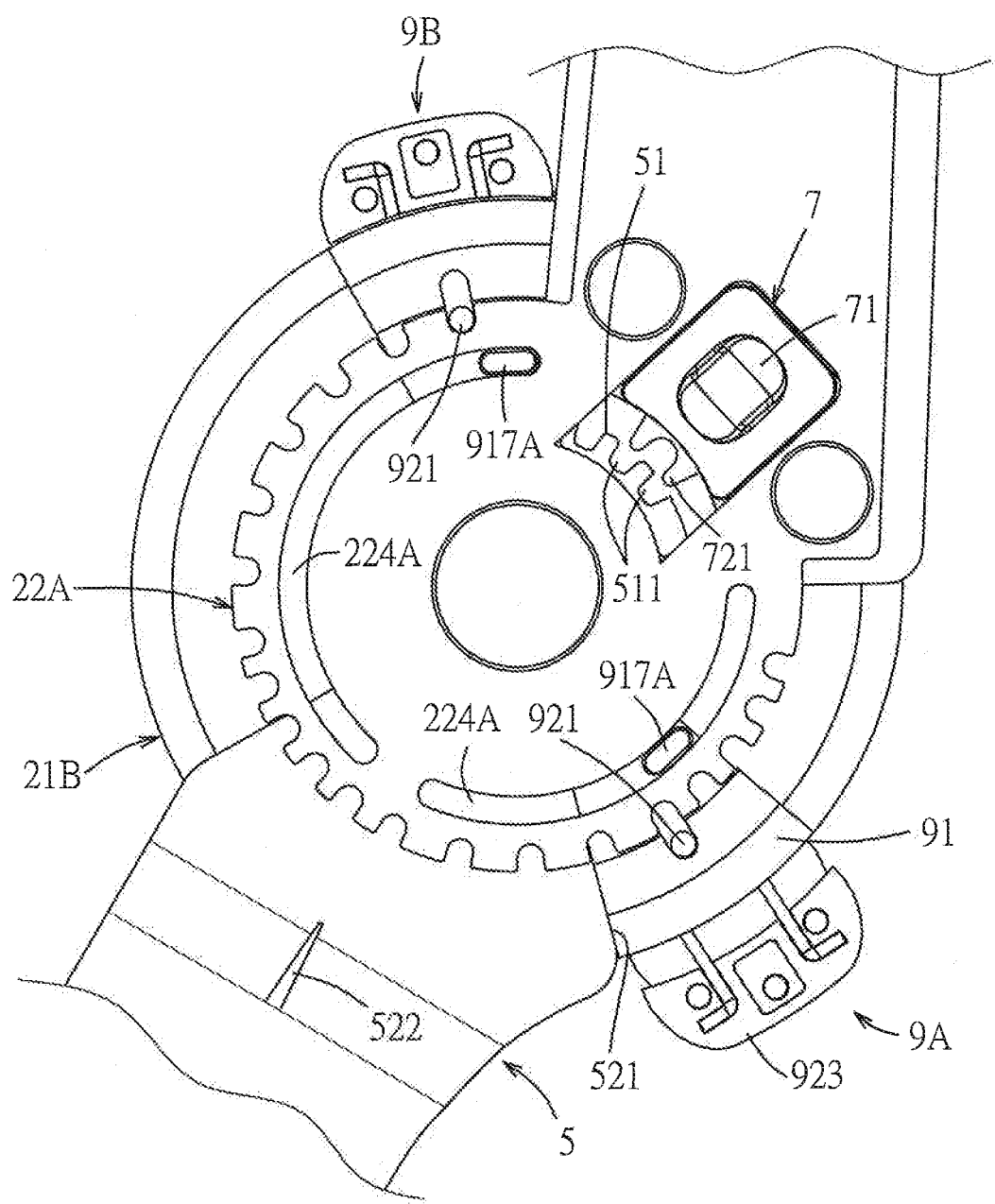
Figure 16:
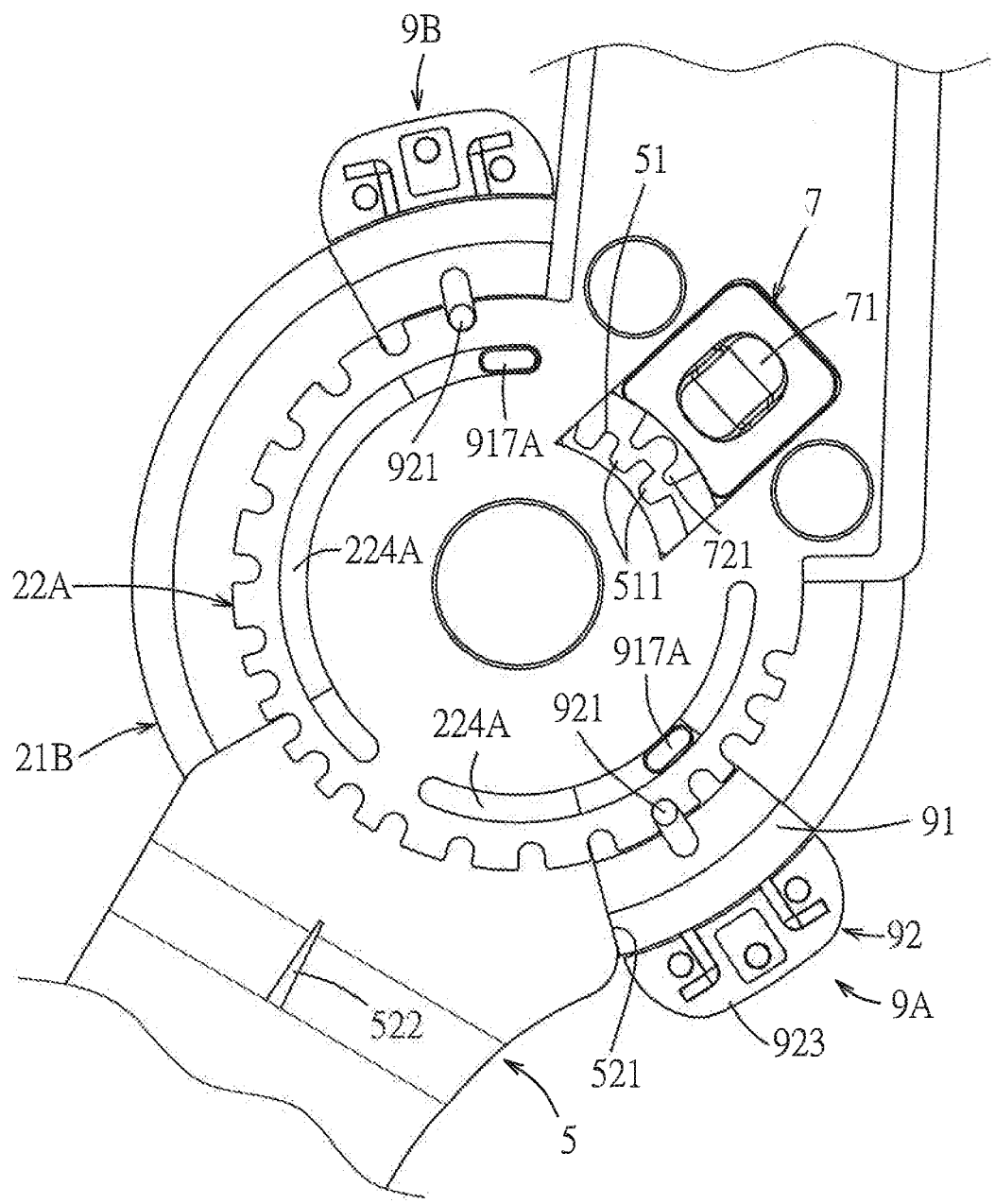

FIGS. 10 and 13 to 16 illustrate consecutive steps for adjusting rotational range of the lower leg plate 5 about the pivot shaft 223 by moving the first position adjusting unit 9A from a first angular position (see FIGS. 13 and 14) to a second angular position (see FIGS. 15 and 16). In operation, the latch bar 71 is moved from the locked position (see FIG. 10) to the unlocked position (see FIG. 13) and the slider body 922 is moved from the engaging position (see FIG. 11) to the disengaging position (see FIGS. 12 to 14), followed by moving the lower leg plate 5 to a desired position (see FIG. 15), where the indicator mark 522 is aligned with a desired one of the indicia 210 on the first cover 21A (referring to FIG. 1 for the relation between the indicator mark 522 and the indicia 210), and then moving the first position adjusting unit 9A from the first angular position (see FIG. 14) to the second angular position (see FIG. 15) to contact an adjacent one of the limiting side edges 521 of the lower leg plate 5. The slider body 922 of the first position adjusting unit 9A is then moved from the disengaging position to the engaging position (see FIG. 16) by the urging force of the coil springs 924.

By receiving the limiting seats 91 and the annular end portion 51 of the lower leg plate 5 in the insertion gap 24 between the first and second catch plates 22A, 22B, each of the limiting seats 91 is substantially disposed at the same level as the annular end portion 51 and does not overlap the annular end portion 51, thereby alleviating the aforesaid drawback of the prior art with respect to the overall thickness of the hinge in the axial direction. In addition, the coil springs 924 do not frictionally contact the pivot shaft 223, thereby eliminating the aforesaid wearing drawback as encountered in the prior art.

While the present invention has been described in connection with that is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A hinge for an orthopedic brace comprising:
   a pivot shaft;
   a lower leg plate pivoted to said pivot shaft;
   an upper leg plate;
   a catch plate secured to an end portion of said upper leg plate and having an annular portion that is sleeved around said pivot shaft and that has a toothed peripheral edge; and
   two position adjusting units, each of which includes a rotatable limiting seat, a limiting pin, and a slider body, said rotatable limiting seat being mounted rotatably on said catch plate and having a seat housing that defines a housing chamber therein and that is formed with a wall slot which extends in a radial direction with respect to said pivot shaft, said slider body being slidably disposed in said housing chamber and being slidable relative to said seat housing in the radial direction between engaging and disengaging positions, said limiting pin extending outwardly of said housing chamber from said slider body through said wall slot so as to be co-slidable with said slider body relative to said seat housing;
   wherein said limiting pin of each of said position adjusting units engages said toothed peripheral edge when said slider body is disposed at the engaging position, thereby preventing rotation of said position adjusting unit relative to said catch plate about said pivot shaft, and is disengaged from said toothed peripheral edge when said slider body is disposed at the disengaging position, thereby permitting rotation of said position adjusting unit about said pivot shaft; and
   wherein said annular portion of said catch plate is formed with two circumferentially extending guiding grooves, said rotatable limiting seat of each of said position adjusting units further having a tongue that protrudes from said seat housing into a respective one of said circumferentially extending guiding grooves, so that rotation of each of said rotatable limiting seats about said pivot shaft is guided along the respective one of said circumferentially extending guiding grooves.

2. The hinge of claim 1, further comprising a cover that is secured to said end portion of said upper leg plate to cover said catch plate and that has an annular portion and a rim portion which protrudes from said annular portion of said cover, said seat housing of said rotatable limiting seat having inner and outer radial ends, two opposite radially extending side walls that extend between said inner and outer radial ends, and a curved bar strip that protrudes from and that cooperates with one of said side walls to define a limiting recess therebetween, said rim portion extending into said limiting recess and abutting against said bar strip of said seat housing of said rotatable limiting seat so as to limit said rotatable limiting seat against movement in the radial direction.

3. The hinge of claim 2, wherein each of said position adjusting units further includes a pull knob that abuts against a peripheral edge of said cover, and a pair of connecting rods that extend from said slider body through said seat housing to connect with said pull knob.

4. The hinge of claim 3, wherein each of said position adjusting units further includes a pair of springs that are sleeved around said connecting rods, that are disposed in said housing chamber, and that abut against said seat housing and said slider body for restoring said slider body from the disengaging position to the engaging position.

5. The hinge of claim 2, wherein said lower leg plate has an end portion that is pivoted to said pivot shaft, and two limiting side edges that are angularly spaced apart from each other, and that are disposed angularly between said rotatable limiting seats of said position adjusting units so that rotation of said lower leg plate about said pivot shaft is limited by said rotatable limiting seats.

6. The hinge of claim 5, further comprising a lock mechanism that includes a latch bar and that is mounted slidably on said cover, said latch bar being provided with a latch protrusion, said end portion of said lower leg plate being formed with a plurality of tooth grooves, said latch bar being slidable in the radial direction between locked and unlocked positions, said latch protrusion engaging a selected one of said tooth grooves when said latch bar is disposed at the locked position, thereby preventing rotation of said lower leg plate relative to said upper leg plate about said pivot shaft, and disengaging said tooth grooves when said latch bar is disposed at the unlocked position, thereby permitting rotation of said lower leg plate relative to said upper leg plate about said pivot shaft.

7. The hinge of claim 6, wherein said latch bar is formed with first and second retaining grooves that are arranged along the radial direction, said cover being formed with a retaining protrusion that protrudes therefrom toward said latch bar, said retaining protrusion engaging said second retaining groove and being disengaged from said first retaining groove when said latch bar is disposed at the locked position, and engaging said first retaining groove and being disengaged from said second retaining groove when said latch bar is disposed at the unlocked position.

8. The hinge of claim 7, wherein said end portion of said upper leg plate is formed with a notch, said latch bar extending through said notch.

9. The hinge of claim 1, wherein said seat housing of said rotatable limiting seat has inner and outer radial ends and two opposite radially extending side walls that extend between said inner and outer radial ends and that are opposite to and that are registered with each other along an axial direction parallel to said pivot shaft, said wall slot being formed in and extending through said side walls.

\* \* \* \* \*